US011058833B2

(12) United States Patent
Holtz et al.

(10) Patent No.: US 11,058,833 B2
(45) Date of Patent: Jul. 13, 2021

(54) USAGE RECORDING SMART LABEL

(71) Applicant: Timestamp Ltd., Hod HaSharon (IL)

(72) Inventors: Arie Holtz, Jerusalem (IL); Aharon Futterman, Netanya (IL)

(73) Assignee: Timestamp Ltd., Hod HaSharon (IL)

( * ) Notice: Subject to any disclaimer, the term of this patent is extended or adjusted under 35 U.S.C. 154(b) by 7 days.

(21) Appl. No.: 16/225,703

(22) Filed: Dec. 19, 2018

(65) Prior Publication Data

US 2019/0125990 A1    May 2, 2019

Related U.S. Application Data

(63) Continuation-in-part of application No. PCT/IL2017/050681, filed on Jun. 19, 2017.
(Continued)

(51) Int. Cl.
*A61M 15/00*    (2006.01)
*G16H 40/63*    (2018.01)
(Continued)

(52) U.S. Cl.
CPC ........ *A61M 15/008* (2014.02); *A61M 15/009* (2013.01); *A61M 15/0083* (2014.02);
(Continued)

(58) Field of Classification Search
None
See application file for complete search history.

(56) References Cited

U.S. PATENT DOCUMENTS

| 5,363,842 A | * | 11/1994 | Mishelevich | ........ A61B 8/0875 128/200.14 |
| 8,539,945 B2 | | 9/2013 | Solomon et al. | |

(Continued)

FOREIGN PATENT DOCUMENTS

| GB | 2506385 A | 4/2014 |
| WO | 0191080 A1 | 11/2001 |

(Continued)

OTHER PUBLICATIONS

International Search Report dated Oct. 2, 2017, International Application No. PCT/IL2017/050681.

*Primary Examiner* — Curtis J King
(74) *Attorney, Agent, or Firm* — Elmore Patent Law Group, P.C.; Joseph C. Zucchero; Carolyn S. Elmore (57) ABSTRACT

A usage recording smart label and inhaler, and methods for detecting, verifying and recording actuation events of the inhaler, are disclosed. The usage recording smart label comprises a capacitive touch sensing plate to detect the presence of an activating body organ such as a hand or finger. The smart label, which may be in the form of a sticker or sticker-like, is attached to a grasping or actuation surface of the inhaler. The smart label may comprise text printed thereon, used as a replacement for an existing printed label. A usage recording method comprises (a) the usage recording smart label detecting an event of proximity of a finger for a given minimal time duration; (b) recording a timestamp of the event in memory of the smart label; (c) communicating stored timestamp data from the memory to an external device; the external device can be configured to display the actuation history.

23 Claims, 6 Drawing Sheets

Related U.S. Application Data (60) Provisional application No. 62/352,022, filed on Jun. 20, 2016.

(51) Int. Cl.
   *G16H 20/10* (2018.01)
   *H03K 17/96* (2006.01)

(52) U.S. Cl.
   CPC ............ *G16H 20/10* (2018.01); *G16H 40/63* (2018.01); *H03K 17/962* (2013.01); *A61M 2205/0227* (2013.01); *A61M 2205/0283* (2013.01); *A61M 2205/13* (2013.01); *A61M 2205/332* (2013.01); *A61M 2205/3306* (2013.01); *A61M 2205/3569* (2013.01); *A61M 2205/3592* (2013.01); *A61M 2205/505* (2013.01); *A61M 2205/52* (2013.01); *A61M 2205/8206* (2013.01); *A61M 2230/63* (2013.01)

(56) References Cited

U.S. PATENT DOCUMENTS

| | | | |
|---|---|---|---|
| 8,807,131 B1* | 8/2014 | Tunnell | A61M 16/0051 128/200.23 |
| 2008/0001737 A1* | 1/2008 | Metry | B32B 7/02 340/540 |
| 2009/0030285 A1 | 1/2009 | Andersen | |
| 2009/0194104 A1* | 8/2009 | Van Sickle | A61M 15/00 128/203.12 |
| 2014/0032243 A1 | 1/2014 | Solomon et al. | |
| 2014/0055589 A1* | 2/2014 | Bangera | G06F 19/3418 348/77 |
| 2014/0182584 A1* | 7/2014 | Sutherland | A61M 15/009 128/200.23 |
| 2014/0188502 A1* | 7/2014 | Defrank | G06F 19/3462 705/2 |
| 2015/0100335 A1 | 4/2015 | Englehard et al. | |
| 2015/0112707 A1 | 4/2015 | Manice et al. | |
| 2015/0174348 A1 | 6/2015 | Tunnell et al. | |
| 2016/0082208 A1* | 3/2016 | Ballam | A61M 16/0003 128/200.14 |
| 2016/0144141 A1* | 5/2016 | Biswas | A61M 15/009 128/200.23 |
| 2016/0325058 A1* | 11/2016 | Samson | G16H 40/67 |
| 2016/0354562 A1* | 12/2016 | Morrison | A61M 15/0001 |
| 2017/0169184 A1* | 6/2017 | Doswell | G06F 19/3456 |
| 2019/0255262 A1* | 8/2019 | Morrison | A61M 15/0001 |

FOREIGN PATENT DOCUMENTS

| | | |
|---|---|---|
| WO | 03020349 A2 | 3/2003 |
| WO | 2015178907 A1 | 11/2015 |
| WO | 2017205824 A1 | 11/2017 |
| WO | 2019180720 A1 | 9/2019 |

\* cited by examiner

USAGE RECORDING SMART LABEL

RELATED APPLICATIONS

This application is a continuation-in-part of International Application No. PCT/IL2017/050681 which designated the United States and was filed on Jun. 19, 2017, published in English, which claims the benefit of U.S. Provisional Application No. 62/352,022, filed on Jun. 20, 2016. The entire teachings of the above applications are incorporated herein by reference.

FIELD OF THE INVENTION

The present invention relates to a disposable usage-recording smart label for inhalers and other hand-held devices, as well as methods for use of the device for monitoring adherence to a treatment regimen.

BACKGROUND OF THE INVENTION

The treatment regimen prescribed for use of inhalers is often not followed properly by many patients, thus preventing those patients from obtaining effective therapy. To this end, various forms of usage monitoring devices were developed through the years, which may be divided into three main categories: (i) motion-based detection—this category typically refers to devices that monitor movement(s) of one part of the inhaler relative to other part(s) of the inhaler; for example, in a metered dose inhaler (MDI) the movement of the canister may be monitored relative to the movement of the part that is pressed with each activation; (ii) sound-based detection—which requires ongoing sampling of the sound and sophisticated digital processing of the sounds detected; and (iii) volume-based detection, e.g., measuring of the air flow through the device.

The aforementioned solutions are relatively complex to manufacture and use, expensive to implement, and can easily exceed the price of the inhaler itself.

U.S. Pat. No. 5,363,842 discloses an intelligent inhaler providing feedback to both patient and medical professional. The device detects how much air is inhaled through an inhaler with what time course as well as certain events such as the triggering of the release of aerosol.

U.S. Pat. No. 8,539,945 discloses a dose counter for a metered dose inhaler comprising a force/pressure sensor.

US 2014/0032243 discloses a method for facilitating the monitoring of adherence to a treatment/therapy regimen requiring administering to the patient at least two drugs using more than a single metered dose inhaler.

There is an unmet need for a low-cost, simple, and optionally disposable, usage monitoring device that can be easily and reversibly attached to inhalers.

SUMMARY OF THE INVENTION

In accordance with some embodiments, there are provided devices, systems and methods for detecting, verifying and recording actuation events of hand-held devices, such as inhalers, utilizing an adherence monitoring device, comprising a proximity sensor to detect the presence of the activating body organ, such as, a hand or a finger. According to some embodiments the monitoring device may be in the form of a sticker or sticker-like. The device is attached to a grasping surface or actuation surface of the inhaler, where said surface is typically touched or held when the inhaler is actuated. Said grasping surface can, for example, be the side or base of the housing of a metered dose inhaler (MDI) or the base of its cylinder, or the side panels or grasping point of a dry powder inhaler (DPI). Advantageously, the disclosed technology enables the same adherence device to be used for multiple types and designs of inhalers—MDIs, DPIs soft mist inhalers (SMIs), or any other type of inhaler—as every type of inhaler has some form of actuation surface or grasping surface. Thus, the device disclosed herein provides a consistent solution for asthma and COPD patients who typically use two different types of inhaler: a reliever inhaler (typically an MDI) and a controller inhaler (typically a DPI). As the device disclosed herein is suitable for multiple inhaler types, this simplifies the implementation of comprehensive monitoring of all the patient's inhalers.

Moreover, the device disclosed herein is simple for manufacturing and use and is of low cost. The simplicity of use makes it transparent to the user, as it does not require any adaption or action beyond holding and activating the inhaler for the purpose of inhalation. Furthermore, due to the long and expensive regulatory process involved in producing a new inhaler, it is beneficial that the device disclosed herein can be implemented as a retrofit or add-on to an existing inhaler, without requiring re-registration of the inhaler product.

In accordance with some embodiments, there are provided methods for using a proximity-based usage recording smart label device with an inhaler, in order to monitor a patient's adherence to a regimen prescribed by a physician. This method involves (a) having said device detect the proximity of a finger to said recording device for a given minimal time duration, thereby reasonably assuming that this reflects a verification of an inhaler-actuation event; (b) record and timestamp said event in the memory of said device, (c) communicate this stored data from the memory within the device to an external device such as a smartphone or a computer, for example via a short-range radio-frequency component or via a wired connection; said external device being configured to be able to display the actuation history on its display. This method enables a physician to see the history of the patient's use of the inhaler at a glance, and derive appropriate conclusions about his adherence. In particular it is important to evaluate whether an unhealthy patient has been compliant but the medications are unsuitable, or whether the chief problem is poor adherence. In the former case the prescription should be changed, whereas in the latter some form of reminder system may be recommended.

In accordance with some embodiments, there is provided a usage recording smart label for attachment to an inhaler, the usage recording smart label comprises at least one proximity sensor, configured to generate a detection signal in response to sensed proximity of a human organ or parts thereof, a communication module, configured to support at least one wired or wireless communication protocol, a memory, a real time clock, a CPU, connected to the memory, the real time clock, the at least one proximity sensor and the communication module, and a power source, configured to supply power to the proximity sensor, the CPU and the real time clock. In accordance with some embodiments, the CPU is configured to retrieve at least one detection signal from the at least one proximity sensor and the time of its occurrence from the real time clock, and record a timestamp corresponding to the at least one detected signal, in the memory.

In accordance with some embodiments, the CPU, the memory and the real time clock are embedded within a microcontroller.

In accordance with some embodiments, the usage recording smart label further comprises a bottom cover comprising an adhesive layer.

In accordance with some embodiments, the at least one proximity sensor comprises at least one capacitive sensor.

In accordance with some embodiments, the at least one capacitive sensor comprises a sensing plate, having at least one capacitive-sensing area, and the usage recording smart label further comprises a touch-sense controller, configured to control the sensing plate.

In accordance with some embodiments, the CPU, the memory, the real time clock and the touch-sense controller are embedded within a microcontroller.

In accordance with some embodiments, the communication module is a wired communication chip.

In accordance with some embodiments, the communication module is a wireless communication chip.

In accordance with some embodiments, the wireless communication chip comprises an NFC chip having an internal memory and an RF antenna.

In accordance with some embodiments, the CPU is configured to retrieve the at least one detection signal from the at least one proximity sensor, and record a timestamp corresponding to the at least one detected signal, in the internal NFC memory.

In accordance with some embodiments, the usage recording smart label further comprises an optical detector, configure to activate the power source, upon first exposure to light.

In accordance with some embodiments, the usage recording smart label further comprises an insulating tab such that the power source is activated upon removal of said insulating tab from the usage recording smart label.

In accordance with some embodiments, the usage recording smart label further comprises an accelerometer configured to sense vibrations of the usage recording smart label simultaneously with the detection signal generation by the proximity sensor.

In accordance with some embodiments, there is provided a method for recording usage of an inhaler, comprising the steps of providing an inhaler comprising the usage recording smart label as described hereinabove, attached thereto, receiving a detection signal having a duration from the proximity sensor, verifying that the duration of the detection signal exceeds a predetermined duration threshold thereby determining a verified actuation event, retrieving the time of the verified actuation event from the real-time clock and recording said time in the memory thereby obtaining a recorded actuation event.

In accordance with some embodiments, the method further comprises initiating operation of the power source, such the power source is configured to supply power source to the CPU, the proximity sensor and the real time clock only after said initiation.

In accordance with some embodiments, the usage recording smart label further comprises an optical detector, and said initiating comprises exposing said optical detector to light.

In accordance with some embodiments, the usage recording smart label further comprises an insulating tab, and said initiating comprises removing said insulating tab.

In accordance with some embodiments, the method further comprises receiving an additional detection signal having a duration from the proximity sensor, determining the time difference between the recorded actuation event and said additional detection signal and verifying that said time difference is higher than a predefined repeated-use threshold prior to recording said additional detection signal in the memory.

In accordance with some embodiments, the usage recording smart label further comprises an accelerometer, and the method further comprises, prior to said retrieving, receiving a vibration signal from the accelerometer simultaneously with said receiving the detection signal and verifying that the vibration signal exceeds a predefined vibration signal threshold, indicative of an actuation event.

In accordance with some embodiments, the usage recording smart label further comprises an accelerometer and the method further comprises, prior to said retrieving, providing at least one vibration pattern indicative of an actuation event, receiving vibration signals from the accelerometer simultaneously with said receiving the detection signal and verifying that the vibration signals match the at least one vibration pattern.

In accordance with some embodiments, the method further comprises providing a remote device, configured to support the communication protocol, generating a communication link between the communication chip and the remote device and transferring usage history recorded in the memory to the remote device.

In accordance with some embodiments, there is provided a system comprising the usage recording smart label, as described hereinabove, and an inhaler. In accordance with some embodiments, the usage recording smart label is attached to said inhaler.

In accordance with some embodiments, the inhaler is a metered-dose inhaler.

In accordance with some embodiments, the inhaler is a dry-powder inhaler.

In accordance with some embodiments, the inhaler is a soft-mist inhaler.

In accordance with some embodiments, the inhaler comprises at least one dose of an inhalable pharmaceutical composition.

In accordance with some embodiments, there is provided use of the aforementioned system for the treatment of a pulmonary disease.

In accordance with some embodiments, the pulmonary disease is asthma or COPD.

In accordance with some embodiments, there is provided a smart-label for affixing to an inhaler, said smart-label comprises at least one sensing plate, configured to generate a detection signal in response to the touch of a human organ or parts thereof, a touch-sense controller, configured to control the at least one sensing plate, a communication module, configured to support at least one wired or wireless communication protocol, a memory, a real time clock, a CPU, connected to the memory, the real time clock, the touch-sense controller and the communication module and a power source, configured to supply power to the proximity sensor, the CPU and the real time clock. In accordance with some embodiments, the CPU is configured to retrieve at least one detection signal from the touch-sense controller and the time of its occurrence from the real time clock, and record a timestamp corresponding to the at least one detected signal, in the memory.

In accordance with some embodiments, the communication module of said smart-label comprises an NFC chip having an internal memory and an RF antenna.

In accordance with some embodiments, the CPU is configured to retrieve the at least one detection signal from the touch-sense controller, and record a timestamp corresponding to the at least one detected signal, in the internal NFC memory.

In accordance with some embodiments, there is provided a method for monitoring inhaler usage comprising providing an inhaler comprising the smart-label as described herein above, attached thereto, receiving a detection signal having a duration from the touch sensor, verifying that the duration of the detection signal exceeds a predetermined duration threshold thereby determining a verified actuation event, retrieving the time of the verified actuation event from the real-time clock, recording said time in the memory thereby obtaining a recorded actuation event.

In accordance with some embodiments, the method further comprises the steps of providing a remote device, configured to support the communication protocol, generating a communication link between the communication chip and the remote device and transferring usage history recorded in the memory to the remote device.

Certain embodiments of the present invention may include some, all, or none of the above advantages. Further advantages may be readily apparent to those skilled in the art from the figures, descriptions, and claims included herein. Aspects and embodiments of the invention are further described in the specification herein below and in the appended claims.

Unless otherwise defined, all technical and scientific terms used herein have the same meaning as commonly understood by one of ordinary skill in the art to which this invention pertains. In case of conflict, the patent specification, including definitions, governs. As used herein, the indefinite articles "a" and "an" mean "at least one" or "one or more" unless the context clearly dictates otherwise.

The following embodiments and aspects thereof are described and illustrated in conjunction with systems, tools and methods which are meant to be exemplary and illustrative, but not limiting in scope. In various embodiments, one or more of the above-described problems have been reduced or eliminated, while other embodiments are directed to other advantages or improvements.

BRIEF DESCRIPTION OF THE FIGURES

Some embodiments of the invention are described herein with reference to the accompanying figures. The description, together with the figures, makes apparent to a person having ordinary skill in the art how some embodiments may be practiced. The figures are for the purpose of illustrative description and no attempt is made to show structural details of an embodiment in more detail than is necessary for a fundamental understanding of the invention. For the sake of clarity, some objects depicted in the figures are not to scale.

In the Figures.

DETAILED DESCRIPTION OF SOME EMBODIMENTS

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure. In the figures, like reference numerals refer to like parts throughout.

The term "patient", as used herein, refers to the user of the devices and methods disclosed herein and include a user having a pulmonary disease or other medical disorder, using any type of inhaler for which the device of the disclosed technology is adapted.

Figure 1A:
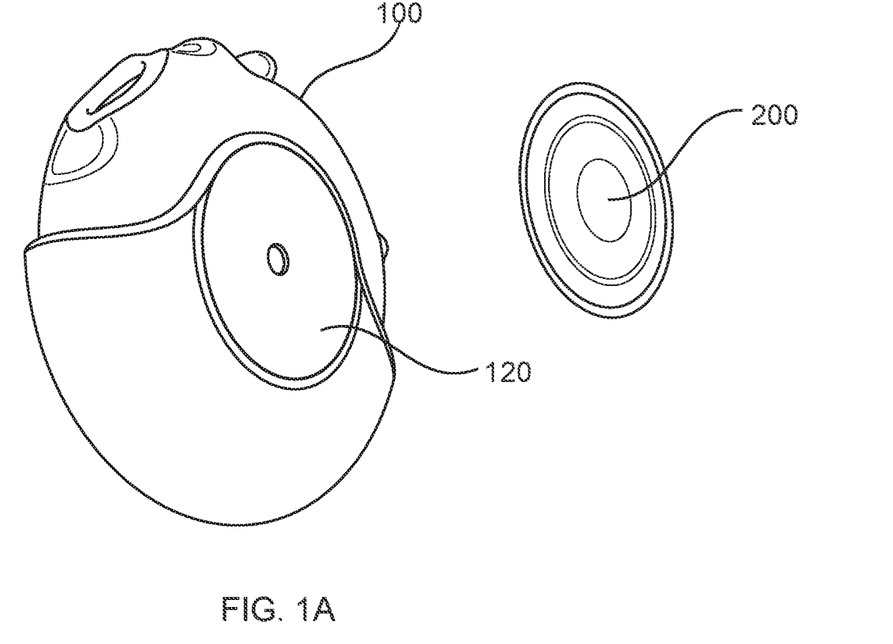
FIG. 1a constitutes an exploded view in perspective of a usage recording smart label and a dry-powder inhaler, in accordance with some embodiments.
Figure 1B:
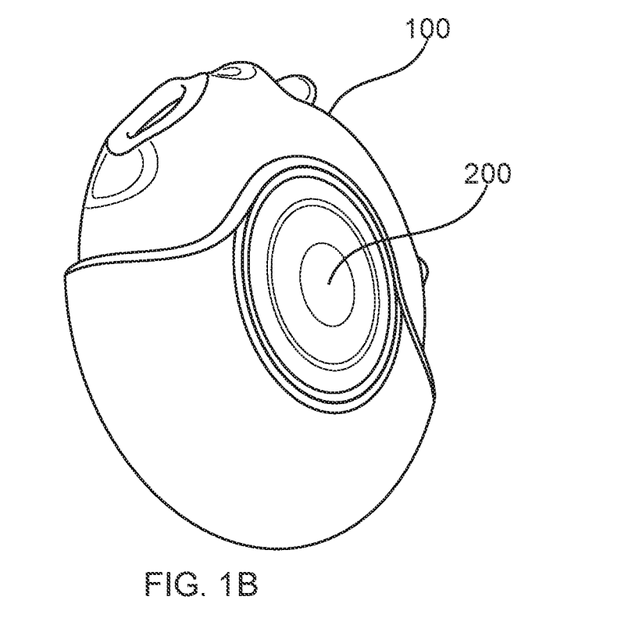
FIG. 1b constitutes a view in perspective of a usage recording smart label attached to a dry-powder inhaler, in accordance with some embodiments.
Figure 1C:
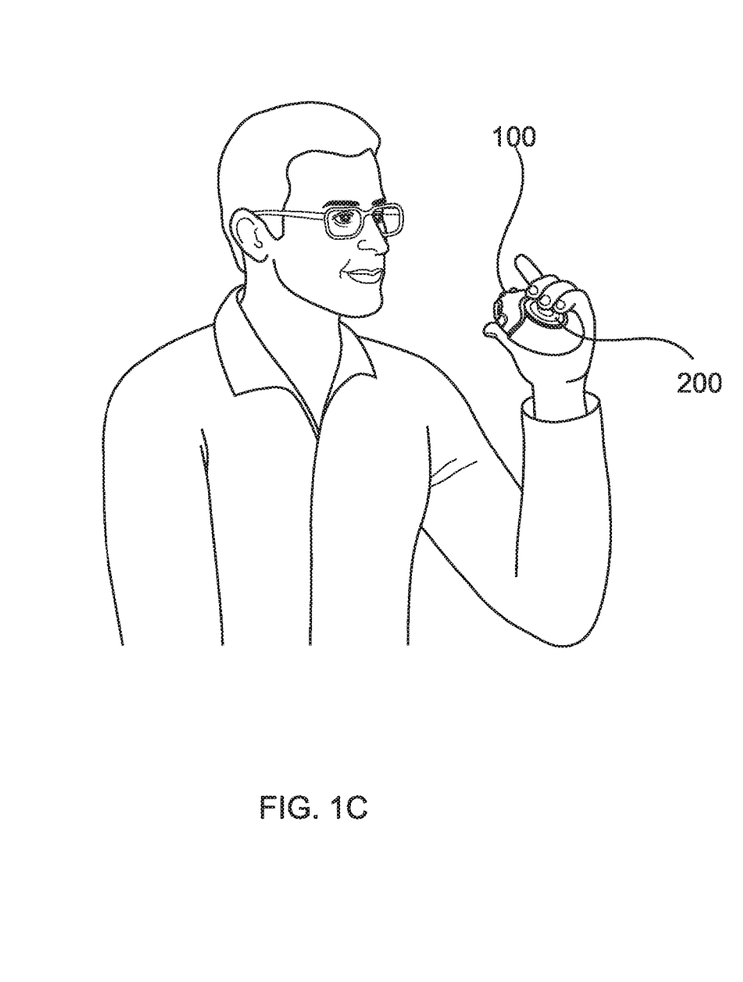
FIG. 1c illustrates a patient using a dry-powder inhaler with a usage recording smart label, in accordance with some embodiments.
Figure 1D:
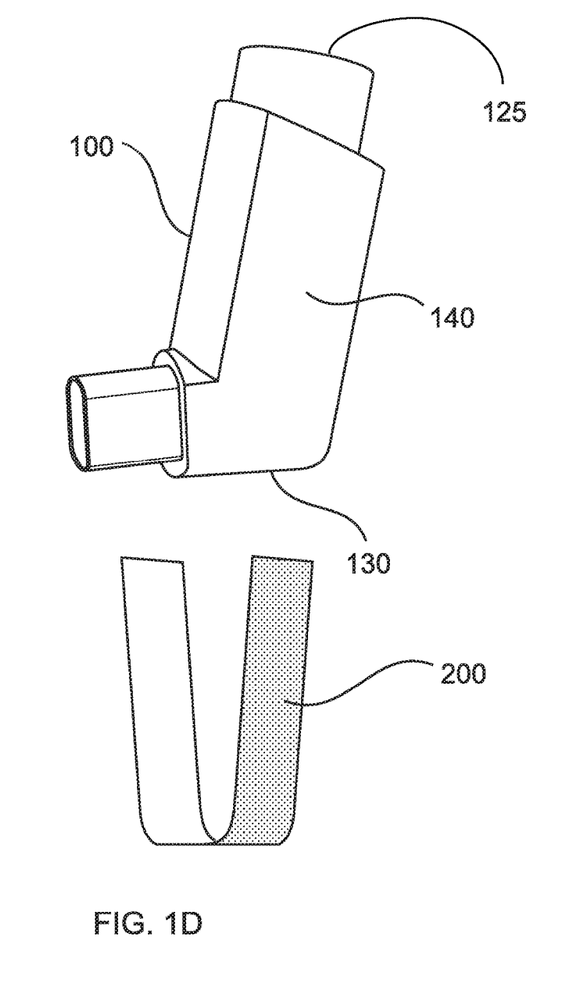
FIG. 1d constitutes an exploded view in perspective of a usage recording smart label and a metered dose inhaler, in accordance with some embodiments.
Figure 1E:
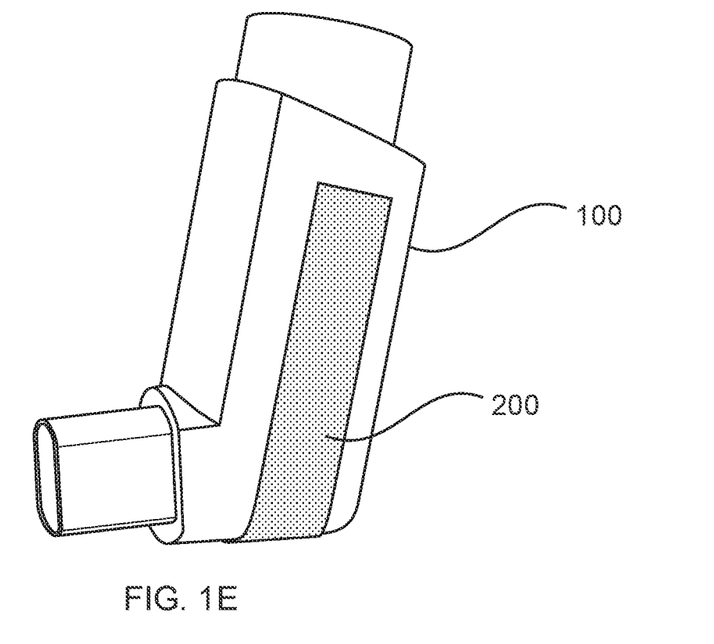
FIG. 1e constitutes a view in perspective of a usage recording smart label attached to a dry-metered dose inhaler, in accordance with some embodiments.
Figure 1F:
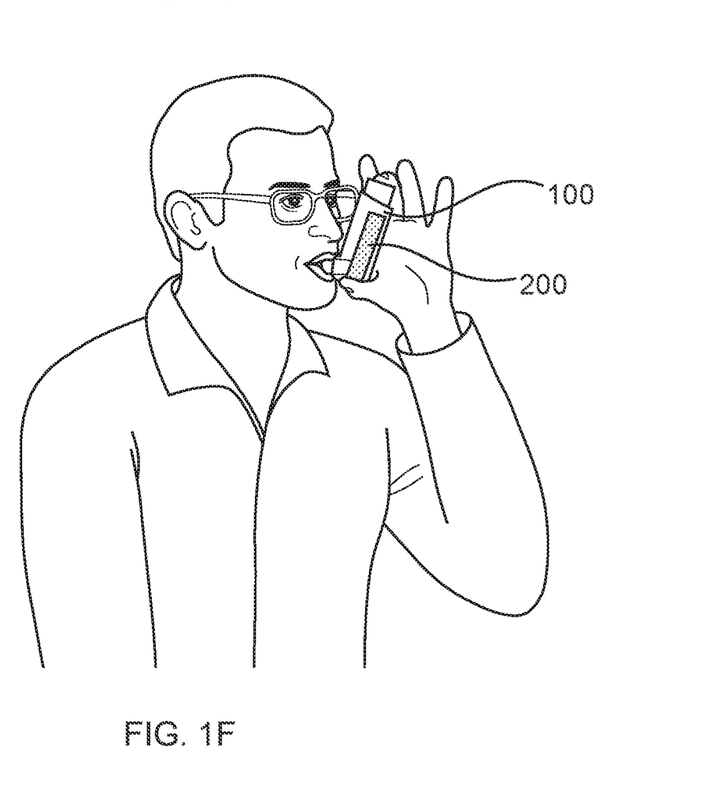
FIG. 1f illustrates a patient using a metered dose inhaler with a usage recording smart label, in accordance with some embodiments.

Reference is now made to FIGS. 1a-1f. A usage recording smart label 200, as disclosed herein, is configured for attachment to an inhaler 100. Inhaler 100 can be any type of a commercially available inhaler, such as, but not limited to: a dry powder inhaler (DPI), or a metered dose inhaler (MDI), SMI, etc. FIGS. 1a and 1d constitute a view in perspective of usage recording smart label 200 prior to attachment to a dry powder inhaler (DPI) and a metered dose inhales (MDI), respectively, in accordance with some embodiments. The DPI inhaler 100 shown in FIG. 1a comprises a side surface 120 suitable for such attachment, whereas the MDI 100 shown in FIG. 1d comprises an upper surface 125, lower surface 130 and sidewalls 140 as potential locations for attaching said device. FIGS. 1b and 1e constitute a view in perspective of usage recording smart label 200 adhered to a side surface 120 of a DPI, and to the bottom surface 130 and sidewalls 140 of an MDI, respectively, in accordance with some embodiments. FIGS. 1c and 1f illustrate a patient using an MDI and a DPI, respectively, with a usage recording smart label 200 attached thereto, in accordance with some embodiments.

Usage recording smart label 200 is configured for attachment to any surface of a hand-held device, such as an inhaler, and is not limited to the adherence configuration presented in FIGS. 1b and 1e. In accordance with some embodiments, usage recording smart label 200 is adhered to upper surface 125 of an MDI inhaler (adhered configuration not shown). Attachment of usage recording smart label 200 can be effected using any type of method known in the art, including but not limited to click-fitting into a recess and adhesion using any form of glue. Usage recording smart label 200 can be designed with a variety of external shapes and dimensions, configured to adapt for attachment to surfaces of inhaler 100, such as a circular shape (see FIGS. 1a and 1b), or a rectangular shape (see usage recording smart label 200 in FIGS. 1d and 1e).

In accordance with some embodiments, usage recording smart label 200 comprises at least one proximity sensor, configured to detect the presence of a human organ or parts thereof, such as a finger. The term "proximity sensor", as used herein, refers to a device that is able to detect the presence of nearby objects without any physical contact. A proximity sensor typically emits an electromagnetic field or a beam of electromagnetic radiation, and looks for changes in the field or return signal. The object being sensed is often referred to as the proximity sensor's target. Different proximity sensor targets demand different sensors. For example, a capacitive or photoelectric sensor might be suitable for a plastic target, whereas an inductive proximity sensor always requires a metal target. In accordance with some embodiments, the at least one proximity sensor comprises at least one capacitive sensor, for example a surface capacitance sensor or a projected capacitance sensor. Capacitive sensors detect anything that is conductive or has a dielectric different from that of air, by detecting the internal frequency change to their capacitive circuit caused by a change in capacitance. In accordance with some embodiments, the at least one capacitive sensor is configured to detect changes in said capacitance detected as a result of the patient grasping or activating the inhaler.

During activation of inhaler 100, a patient typically places at least one finger on a surface of inhaler 100, such as side surface 120 of MDI 100 (FIG. 1c) or lower surface 130 of DPI 100 (FIG. 1f), wherein said finger remains in contact with usage recording smart label 200 for a minimal time duration. The minimal time duration of contact which is indicative of an actuation can vary according to inhaler type. In accordance with some embodiments, minimal time duration is at least 1 second for MDI or DPI type inhalers. In order to verify that a signal detection is indeed indicative of an actual actuation signal, i.e. to lower false positive actuation detections, a duration threshold can be defined. In accordance with some embodiments, the duration threshold is in the range of 1 to 5 seconds. Thus, a detection signal is recorded as an actuation event only if the time passing from the instant of event detection by the proximity sensor, defined as the detection signal duration, exceeds said duration threshold. In accordance with some embodiments, in order to further lower false positive detections, the device further comprises an accelerometer, configured to verify that the device is experiencing motion simultaneously with signal detection by the proximity sensor.

Figure 2A:
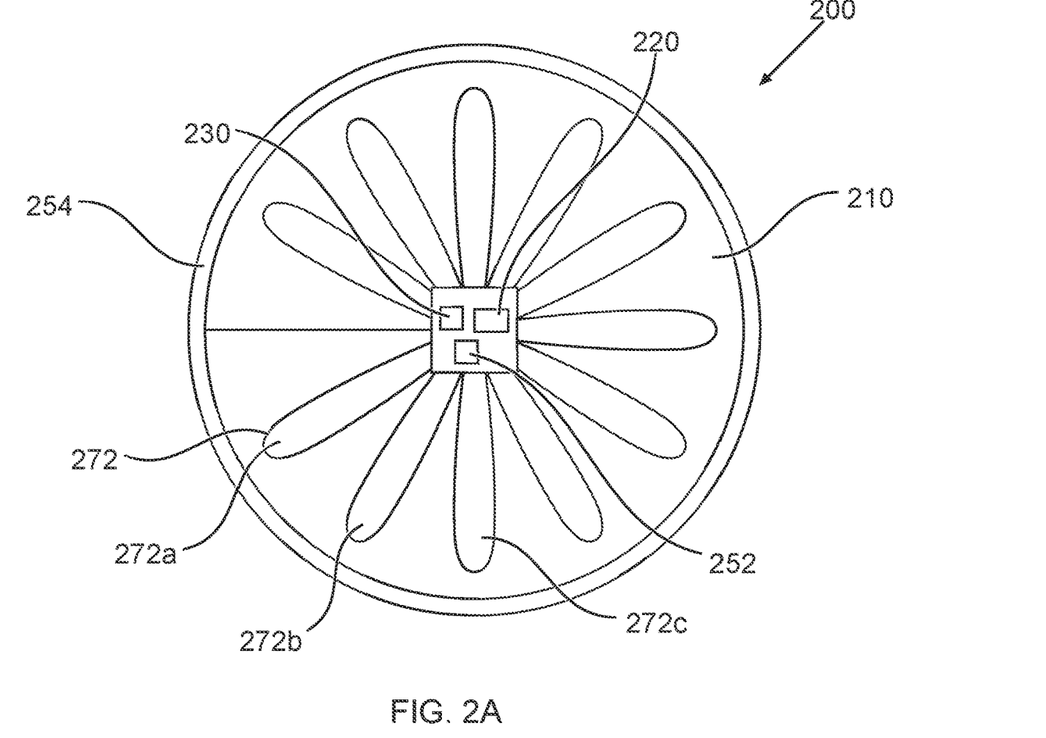
FIG. 2a constitutes a top view of a usage recording smart label, in accordance with some embodiments.
Figure 2B:
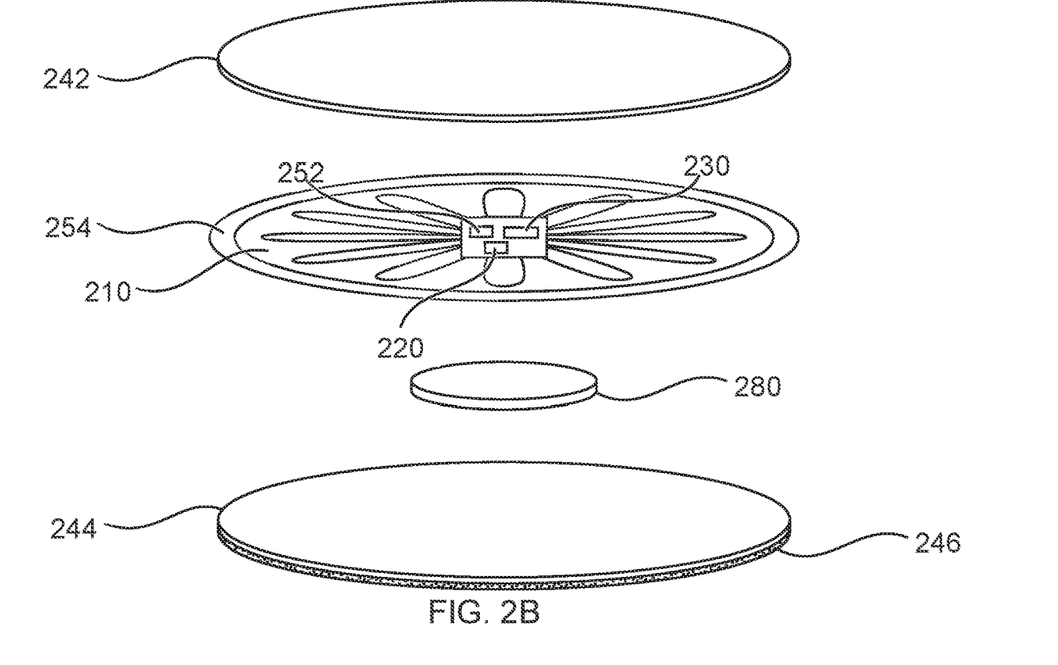
FIG. 2b constitutes an exploded view in perspective of a usage recording smart label, in accordance with some embodiments.

Reference is now made to FIGS. 2a-2b. FIGS. 2a and 2b constitute a top view and an exploded view in perspective of a usage recording smart label 200, respectively, in accordance with some embodiments. Usage recording smart label 200 comprises printed circuit board 210 and power source 280. In accordance with some embodiments, usage recording smart label comprises top cover 242 (visible in FIG. 2b, yet removed from FIG. 2a for clarity) configured to cover printed circuit board 210, and bottom cover 244. Printed circuit board 210 comprises a central processing unit (CPU), a memory, a real-time clock (RTC), a proximity sensor, and a communication module 250. In some embodiments, the CPU, the memory and the RTC are embedded within microcontroller 220. In accordance with some embodiments, the proximity sensor comprises a capacitive sensor. In accordance with some embodiments, usage recording smart label 200 further comprises a touch-sense controller (not shown in FIGS. 2a-b), and the capacitive sensor comprises a sensing plate 272 controlled by a touch-sense controller (not shown in FIGS. 2a-b). In accordance with some embodiments, the touch-sense controller is included in microcontroller 220. In accordance with some embodiments, sensing plate 272 comprises at least one printed capacitive-sensing areas (such as printed capacitive-sensing areas 272a-c in FIGS. 2a-b). Power source 280 can be located either between printed circuit board 210 and bottom cover 244, or embedded within a socket of printed circuit board 210 (not shown).

The terms "circuit", "circuitry" and "printed circuit board", as used herein, are interchangeable, and refer to at least one path in which electrical current flows between electrically operated components.

The term "microcontroller", as used herein, refers to a single chip device which includes a plurality of modules which may be collected onto a single chip in order to perform various computer-related functions. In particular, microcontroller 220 can include a CPU module, a memory module and a real-time clock module, together with additional integral circuit modules. An example of a microcontroller is STM32L052 from ST Microelectronics (Geneva, Switzerland), which is an ARM-based microcontroller comprising an RTC and a TSC.

The term "CPU", as used herein, refers to a computing component that interprets and executes instructions.

The term "memory", as used herein, refers to any suitable data storage component, including volatile memory types such as random access memory, DRAM, SDRAM, and others.

As stated hereinabove, in accordance with some embodiments, the microcontroller 220 further comprises a touch-sense controller. The terms "touch-sense controller" and "TSC", as used herein, are interchangeable, and refer to a circuit for sensing capacitance changes as detected at sensing plate 272.

In accordance with some embodiments, microcontroller 220 comprises a set of software algorithms configured to handle monitoring, detection and recording of actuation events. According to some embodiments, a repeating-use threshold is defined as a period of time during which only a single verified detection signal is recorded as an actuation event. The software algorithms are configured to ignore all additional detection signals beyond a previously recorded event during a predefined repeating-use threshold, such that any spurious handling occurring during that repeating-use threshold period will not be recorded as additional actuation events. According to some embodiments, said repeating-use threshold is in the range of between 10 minutes and 10 hours. According to some embodiments, said repeating-use threshold is in the range between 30 minutes and 90 minutes.

The term "software algorithms", as used herein, refer to a sequence of instructions configured for execution by a microcontroller 220. Software algorithms can include a subroutine, a function, a procedure, an object method, an object implementation, in an executable application, an applet, a servlet, a source code, an object code, a shared library/dynamic load library and/or other sequence of instructions designed for execution by a processing system.

In accordance with some embodiments, usage recording smart label 200 comprises adhesive layer 246, configured to affix usage recording smart label 200 to external surfaces of various types of inhaler 100, such as an MDI or a DPI.

In accordance with some embodiments, adhesive layer 246 comprises a homogenous continuous layer covering all of the area of the lower face (not numbered) of bottom cover

244. In accordance with some embodiments, adhesive layer 246 comprises a homogenous continuous layer covering a portion of the lower face of bottom cover 244. In accordance with some embodiments, adhesive layer 246 comprises a non-homogenous layer, arranged as adhesive stripes spaced apart from one another along the lower face of bottom cover 244. In accordance with some embodiments, adhesive layer 246 comprises a non-homogenous layer, arranged as adhesive speckles scattered along the lower face of bottom cover 244.

In accordance with some embodiments, top cover 242 and bottom cover 244 are configured to be flexible and resilient, such that placement of usage recording smart label 200 on a selected surface of inhaler 100 does not damage printed circuit board 220.

The communication module comprises electronic communication systems and methods for usage recording smart label 200, including a wired and wireless link. Said wireless link can incorporate any suitable wireless connection technology known in the art, including but not limited to NFC, Wi-Fi (IEEE 802.11), Bluetooth, other radio frequencies, Infra-Red (IR), GSM, CDMA, GPRS, 3G, 4G, W-CDMA, EDGE or DCDMA200 and similar technologies. Additionally, the systems for electronic communication may include a wired connection or various ports, including RS-232, or other standard communication technology known in the art. In accordance with some embodiments, said communication module comprises a near-field communication (NFC) chip 252 and a radio-frequency (RF) antenna 254.

In accordance with some embodiments, power source 280 comprises a battery. In accordance with some embodiments, power source 280 comprises a lithium-based coin cell, such as a model CR2012, configured to provide long-term power over the shelf life of the inhaler product. It is desirable that the proximity sensor chosen to be implemented in usage recording smart label 200 have very low drain, so as to minimize the drain on the battery. In this way, the main functionality that needs to keep running when the device is in standby mode is the function of proximity sensing and the real-time clock.

Usage recording smart label 200 is advantageously configured to meet two opposing design criteria: keeping the device small and affordable, while at the same time providing sufficient battery power to last for the lifetime adapted to match the duration of usage of the inhaler it is configured to adhere to. Device lifetime comprises shelf life, defined as the time on the shelf prior to first usage, followed by actual usage period after activation of the power source of the device. In accordance with some embodiments, shelf life is in the range of 1 to 4 years. In accordance with some embodiments, shelf life is in the range of 2 years to 3 years. In accordance with some embodiments, actual usage period is in the range of 1 month to 2 years. In accordance with some embodiments, minimization of power drain during device lifetime is achieved by an initialization mechanism, said initialization mechanism is configured to provide power to the components of usage recording smart label 200 only from the moment it is extracted from its packaging.

In accordance with some embodiments, power source 280 activation comprises the steps of placing an insulating tab between two contacts (not shown) leading to power source 280, such as a battery, such that the removal of said insulating tab leads to direct connectivity between these contacts. In accordance with some embodiments, at least one of said contacts is spring-loaded to displace towards the other contact upon removal of said tab. In accordance with some embodiments, the tab is attached to packaging (not shown) of usage recording smart label 200, such that the tab is automatically removed on the instant of removing usage recording smart label 200 from its packaging, thereby resulting in activation of power source 280.

As used herein, the terms "power" and "energy" are interchangeable, and refer to electrical energy such as electricity. Energy is quantified in e.g. Watt-hour, Ampere-hour, or Joule.

In accordance with some embodiments, usage recording smart label 200 comprises optical sensor 230 as an alternative power source 280 activation mechanism, configured to activate power source 280 upon first exposure to light. In accordance with some embodiments, package (not shown) of an inhaler equipped with usage recording smart label 200, comprising optical sensor 230, is configured to block light exposure to the contents of said package. In accordance with some embodiments, the package comprises aluminum foil, configured to allow exposure of said optical sensor to light only upon removal of said inhaler from the package. In accordance with some embodiments, package of a usage recording smart label 200 (without an inhaler), comprising optical sensor 230, is configured to block light exposure to the contents of said package. In accordance with some embodiments, the package comprises aluminum foil, configured to allow exposure of said optical sensor to light only upon removal of usage recording smart label 200 from the package. An example of an optical sensor can include PT19-21C from Everlight Electronics Co., Ltd.

In accordance with some embodiments, minimization of power drain during smart label lifetime is achieved by limiting power-source 280 drain in stand-by mode between activations of inhaler 100.

The expected number of activations of inhaler 100 varies according to inhaler type. In accordance with some embodiments, the number of activations varies in the range of 10 to 600. In accordance with some embodiments, the number of activations varies in the range of 100 to 200. In accordance with some embodiments, an inhaler is activated no more than once a day, over a period of between 1 month and 6 months. In accordance with some embodiments, a single activation of an inhaler lasts between 10 milliseconds and 10 seconds. In accordance with some embodiments, a single activation of an inhaler lasts between 100 milliseconds and 3 seconds. It is apparent that an inhaler, assumed to be activated at a frequency of no more than once a day for a period of up to 10 seconds per activation, means that circuit 210 remains in stand-by mode during the vast bulk of the time. Therefore, there is great importance in being able to minimize power-source drain in this mode. In accordance with some embodiments, capacitance reading during stand-by mode is taken twice per second, so as not to miss an actuation event of at least one second in duration. If for example, taking a capacitance reading requires minor current drain (250 µA), multiplying this drain by a period of between 3 to 6 months of being in stand-by mode, a battery having a 30 mAh capacity can be sufficient.

Advantageously, the drain incurred during the stand-by mode when using the capacitance-based approach of the current invention is expected to be much less than would be the case were a different sensing technology (such as an ongoing audio analysis) to be employed.

Figure 3A:
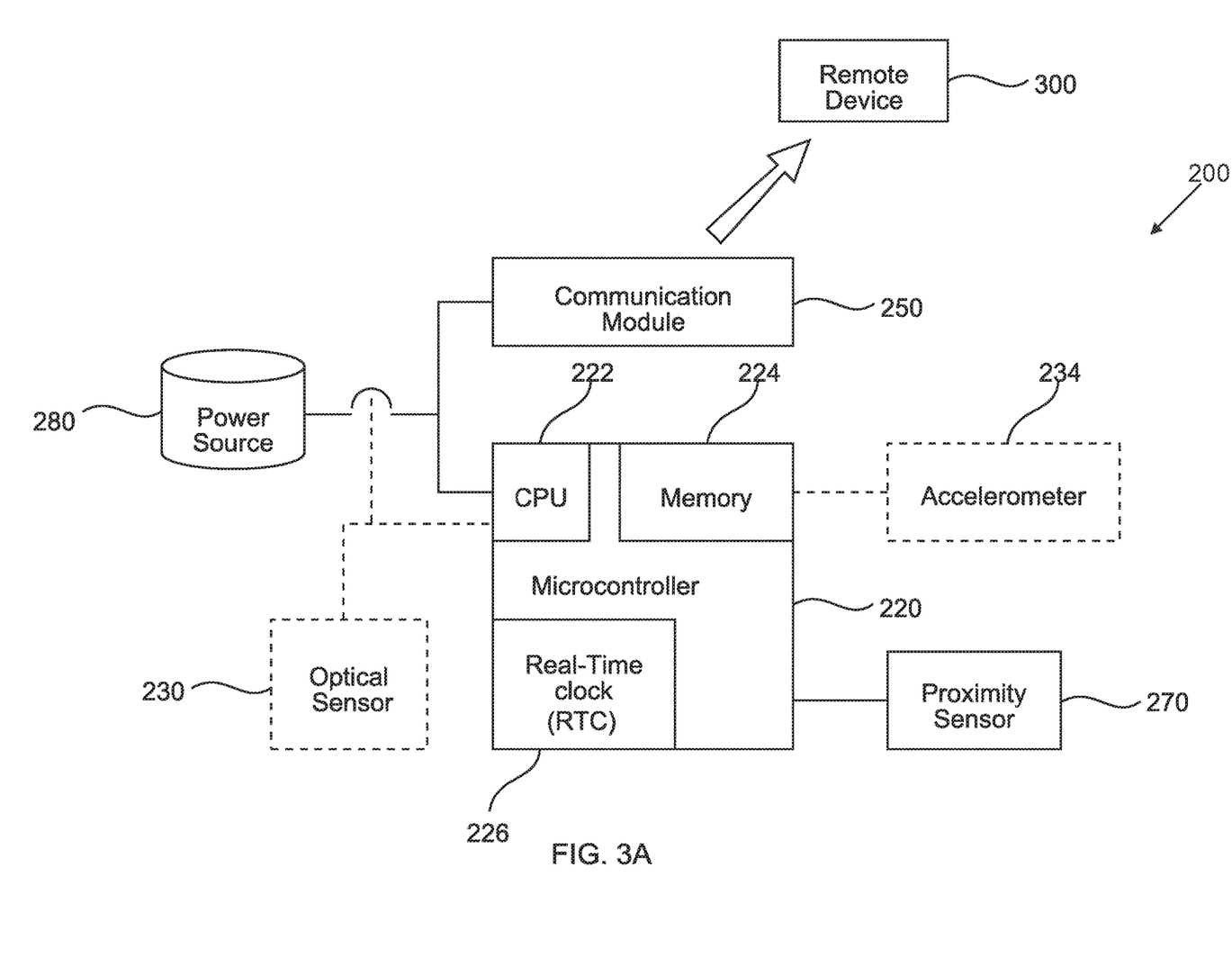
FIG. 3a constitutes a block diagram of internal and external connectivity of components of a usage recording smart label, in accordance with some embodiments.
Figure 3B:
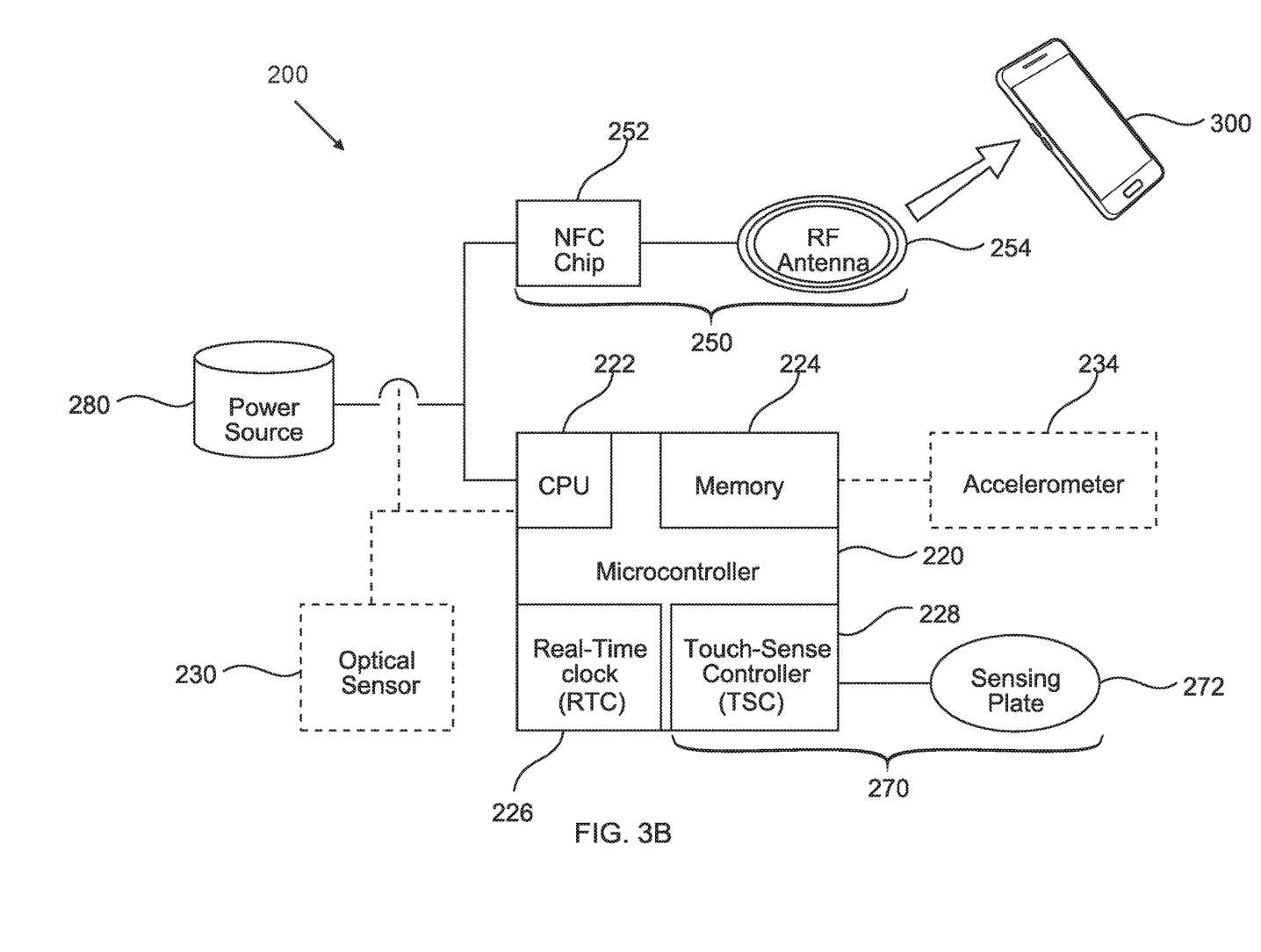
FIG. 3b constitutes a block diagram of internal and external connectivity of components of a usage recording smart label, in accordance with some embodiments.

Reference is now made to FIGS. 3a-3b. In the figures, dashed lines indicate optional components, in accordance with some embodiments. FIG. 3a constitutes a block diagram of internal and external connectivity of components of a usage recording smart label 200, in accordance with some embodiments. In the configuration presented in FIG. 3a, usage recording smart label 200 comprises power source 280, microcontroller 220, proximity sensor 270 and communication module 250. Microcontroller 220 comprises CPU 222, memory 324, and real-time clock (RTC) 226. In accordance with some embodiments, usage recording smart label 200 further comprises optical sensor 230 configured to activate power source 280 the moment optical sensor 230 is first exposed to light, thereby initiating RTC 226 and entering stand-by mode.

When a proximity signal is detected by proximity sensor 270, RTC 226 starts to measure time passing from the moment of signal detection in order to differentiate a passing hand or finger from one which settles on the smart label 200 and remains in its proximity for a minimal time duration. Detection signal duration in excess of a predefined duration threshold is assumed to correlate to an inhaler actuation event. In accordance with some embodiments, duration threshold is 1 second for at least one type of inhaler 100.

In accordance with some embodiments, usage recording smart label 200 further comprises an accelerometer 234, such that once a signal is detected by proximity sensor 270, microcontroller 220 simultaneously seeks for the typical inhaler vibration signal, detected via accelerometer 234.

In accordance with some embodiments, once an actuation event is confirmed, the timestamp of said event is recorded in memory 224, for future retrieval. In accordance with some embodiments, accelerometer 234 comprises pattern recognition algorithms to determine actual usage of inhaler 100. An example of pattern recognition algorithm can determine that inhaler 100 is in use when at least one vibration signal measured by accelerometer 234 exceeds a predefined vibration threshold.

In accordance with some embodiments, different vibration patterns, which can be detected by accelerometer 234, are indicative of actuation events of different types of inhaler 100. Thus, another pattern recognition algorithm is when vibration signals measured by accelerometer 234 match at least one predefined vibration pattern. In accordance with some embodiments, both acceleration and capacitance data are used to determine whether inhaler 100 is in use, thereby minimizing false positive detections resulting purely from the capacitive sensing.

The term "timestamp", as used herein, refers to a record which comprises at least one of: date and time of event detection. In accordance with some embodiments, a timestamp record does not comprise an absolute date and time, but rather the amount of time that passed from one of: a previous event, the moment of smart label 200 initiation, or any other preset event, such that date and time can be calculated based on said amount of time.

The term "pattern", as used herein, relates to an arrangement of signals, which can be expressed, for example, by a combination of frequencies and amplitudes of said signals.

The term "match," as used herein, refers to either an exact match between measured vibration signals and a predefined vibration pattern, or a matches within a tolerance threshold of 80% between measured vibration signals and a predefined vibration pattern.

In accordance with some embodiments, communications module 250 is configured to support wired or wireless communication protocols, such as Bluetooth wireless protocol, an ANT protocol, or a ZigBee protocol. In accordance with some embodiment, communication module 250 is configured to transfer timestamp data from memory 224 to remote smart label 300. In accordance with some embodiments, communications module 250 can be implemented within a chip.

FIG. 3b constitutes a block diagram of internal and external connectivity of components of a usage recording smart label 200, in accordance with some embodiments. In the configuration presented in FIG. 3b, usage recording smart label 200 comprises power source 280, microcontroller 220, sensing plate 272, and communications module 250. Microcontroller 220 comprises CPU 222, memory 224, RTC 226 and TSC 228, configured to control sensing plate 272. Sensing plate 272, controlled by TSC 228, serves in this configuration as capacitive sensor 270.

In accordance with some embodiments, communications module 250 comprises NFC chip 252 and RF antenna 254, supporting a low-drain near field communication (NFC) protocol. NFC chip 252 is configured to operate in passive mode, not being connected to power source 280, thereby preserving power-source energy. In this mode of operation, the NFC communications module 250 is configured to harvest energy from incoming RF emissions to power the NFC chip's 252 interface and RF transmissions. In accordance with some embodiments, incoming RF emissions originate from a signal reader, such as remote device 300. Advantageously, when operating in passive mode there is no need to maintain power to the NFC chip 252 on an ongoing basis, thereby prolonging the required life duration of power source 280. An example of an NFC chip 252 is M24SR64 from ST Microelectronics.

In accordance with some embodiments, microcontroller 220 is configured to sample the capacitance of capacitive sensor 230 at predefined intervals. In accordance with some embodiments, capacitance of sensor 230 is measured at intervals of between 100 milliseconds and 1 second. If a significant change in capacitance is detected, the sampling rate is increased until the actuation event concludes. In accordance with some embodiments, the sampling rate is increased to more than 2 times per second. If the duration of this event exceeds a pre-defined threshold, then the event is timestamped and recorded in memory 224. In accordance with some embodiments, pre-defined threshold is at least 2 seconds. Timestamped data is recorded in memory 224 for each detected event.

In accordance with some embodiments, NFC chip 252 comprises an internal NFC memory (not shown), such that timestamped data is recorded in said internal NFC memory, either instead of or in addition to being recorded in memory 224 of microcontroller 220.

NFC communication protocol is supported by many common remote devices. When a remote device 300, is within range of usage recording smart label 200, communication chip 250 can be configured to receive power from remote device 300, and a wireless communication link may be established between remote device 300 and communication chip 250.

In accordance with some embodiments, information transferred to remote device 300 comprises a history of inhaler use. An application can be installed on remote device 300, configured to display such data, thereby presenting a use history of inhaler 100 over time. In accordance with some embodiments, inhaler 100 is a controller type inhaler, such that use history should present at least a single daily use if the patient is compliant.

The terms "use history" and "history of inhaler use", as used herein, are interchangeable, and refer to a series of recorded timestamped events.

In accordance with some embodiments, an application can associate downloaded data with additional information obtained from third party sources.

The term "remote device", as used herein, refers to a device which supports communication protocols that enable communication with communication chip 250 of usage recording smart label 200. The remote device can be, for example, a cell telecommunication device, like a cell phone or a smartphone or a tablet or a connected watch adapted to wirelessly communicate with the smart label. The remote device can also, be alternatively or comprise simultaneously, a personal computer, with internet link or not, for example being then able to communicate with other personal computers.

Events related to communication module 250 can also be recorded in the memory 224 of microcontroller 220 or an internal memory of the NFC chip 252, such as to log the time when a physician has last read the history of actuation events. This can enable an app installed on remote device 300 to present a potential change in patient usage patterns, following the patient's previous visit to the physician.

FIG. 3b constitutes a block diagram of internal and external connectivity of components of a usage recording smart label 200, including accelerometer 234 in accordance with some embodiments.

For a rescue type inhaler, the usage data should show just occasional use, or none at all if the patient has not had any asthma attacks during the period covered. Use history of both controller and reliever inhalers used by a single patient, together, can present comprehensive data regarding whether the patient's asthma or COPD has been controlled during the period covered.

The method of measuring compliance using smart label 200 of the present disclosed technology therefore comprises the steps of: detecting inhaler 100 use history, based on ongoing recording of actuation events defined by proximity of a patient's fingers to the actuation or grasping location on the inhaler, serving as the surface of inhaler 100 to which smart label 200 is adhered, downloading said use history over a link established between communications module 250 (e.g., comprising NFC chip 252) to an external device such as a remote device 300, wherein said use history can be displayed on a display of said external device 300 in order to assess patient's compliance.

Advantageously, the use of smart label 200 of the disclosed technology does not require any change in patient behavior, as he/she continues to use the inhaler in the same manner as without smart label 200, without requiring additional actions such as moving a usage monitoring smart label from inhaler to inhaler. This is important as, where a patient is required to change his/her behavior, such requirements may introduce a very negative effect on patient's compliance. Additionally, if a short-range communication protocol such as NFC is used to communicate the data externally, the need to set up Bluetooth pairing is obviated.

In accordance with some embodiments, usage recording smart label 200 is configured to replace an existing label of an inhaler, such that top cover 242 can contain the text that was printed on said replaced label, making it a one-for-one replacement for an existing label, but one which is configured to detect and record actuation events. The text on top cover 242 may comprise a drug name, dosage information, and/or disclosures required by law or regulations.

In accordance with some embodiments, usage recording smart label 200 is configured to serve as a smart-label 200 for an inhaler 100. The term "smart-label", as used herein, refers to a label which replaces or provides additional functionality to an existing label of a product. Examples of smart labels include, but are not limited to, RFID tags on clothing or other consumer products and time-temperature indicators (TTI) on time-sensitive products, such as food packages and blood bags. Smart-labels provide a level of functionality that would not ordinarily be provided by a plain paper label, as they provide information about the freshness of a product or a link (via, for example, mobile devices such as a smartphone) to access much more extensive information about the product than would be possible to print on a simple label.

Smart-label 200 of the disclosed technology is intended to replace a non-smart existing label on an inhaler, by adding to the label functionality relating to the handling or grasping history of the product to which the label is affixed. Such a label may include a paper or synthetic paper (for example, TYVEK®), on which information concerning the content or use of the inhaler is printed.

Smart-label 200 comprises a circuit board 210 and at least one sensing plate 272. Circuit board 210 comprises CPU 222, memory 224, RTC 226 and a touch-sense controller (TSC) 228. Said circuit board 210 is configured, through CPU 222, to store in memory 224 a history of handling events as detected at the at least one sensing plate 272 connected via TSC 228 to CPU 222. Said event history can be stored in regular memory 224 or within the internal memory of an NFC chip 252, for simple wireless communication. The at least one sensing plate 272 along with TSC 228 can use any sensing method known in the art—including but not limited to: capacitance sensing, force-sensitive resistance and piezo electric sensing—providing that the sensing method is capable of sensing the touch of a hand or a finger against said smart-label 200. Under control of CPU 222, the duration of said sensed touch is measured (as described hereinabove), such that beyond a pre-defined duration threshold this extended-duration touching is recorded as a handling event, presumably associated with the activation of inhaler 100. In accordance with some embodiments, the duration threshold is in the range of 1 to 5 seconds. As such a touching process may happen numerous times while just one inhalation is being performed, smart-label 200 of the disclosed technology only timestamps and records one such event for a predefined time period following the event detection, defined as a repeating-use threshold. In accordance with some embodiments, said repeating-use threshold is in the range between 30 minutes and 60 minutes. As described hereinabove, a communications module 250 such as an NFC chip 252 enables the contents of the internal NFC memory to be communicated to an external device 300 in order to enable a physician to later monitor the use of the inhaler.

In some embodiments, printed circuit board 210 is a flexible PCB. Power source 280 can be a flexible thin-film battery (e.g., model CP102015 lithium/manganese dioxide battery from Guangzhou Markyn Battery Co., Ltd.; Nancun Town, Panyu District, Guangzhou P.R.C.). Flexibility of printed circuit board 210 and/or power source 280 can further enhance adaptability of usage recording smart label 200 to different designs of inhalers, by facilitating shape-conformance of usage recording smart label 200 for adhesion to inhalers with different exterior surface curvatures.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. No feature described in the context of an embodiment is to be considered an essential feature of that embodiment, unless explicitly specified as such.

Although the invention is described in conjunction with specific embodiments thereof, it is evident that numerous alternatives, modifications and variations that are apparent to those skilled in the art may exist. It is to be understood that the invention is not necessarily limited in its application to the details of construction and the arrangement of the components and/or methods set forth herein. Other embodiments may be practiced, and an embodiment may be carried out in various ways. Accordingly, the invention embraces all such alternatives, modifications and variations that fall within the scope of the appended claims.

The invention claimed is:

1. A usage recording smart label for attachment to an inhaler, comprising:
   at least one capacitive touch sensing plate, configured to generate a detection signal in response to sensed proximity of a human organ or parts thereof;
   a touch-sense controller, configured to control the capacitive touch sensing plate;
   a communication module, configured to support at least one wired or wireless communication protocol;
   a memory;
   a real time clock;
   a CPU, connected to the memory, the real time clock, the at least one capacitive touch sensing plate and the communication module; and
   a power source, configured to supply power to the touch-sense controller, the CPU and the real time clock,
   wherein the CPU is configured to retrieve the detection signal from the touch-sense controller, verify that the duration of the detection signal exceeds a predetermined duration threshold, retrieve the time of its occurrence from the real time clock, and record a timestamp at said retrieved time of an actuation event of said inhaler, corresponding to the verified detection signal, in the memory; and
   wherein said usage recording smart label is in the form of a sticker conformable to an external surface of an inhaler.

2. The usage recording smart label according to claim 1, wherein said power source comprises a flexible thin-film battery.

3. The usage recording smart label according to claim 1, further comprising an adhesive layer configured for said attachment of said usage recording smart label to an inhaler.

4. The usage recording smart label according to claim 3, further comprising a bottom cover, wherein at least a portion of a lower face of said bottom cover comprises said adhesive layer.

5. The usage recording smart label of claim 1, wherein the CPU and one or more of the memory, the real time clock and the touch-sense controller are embedded within a microcontroller.

6. The usage recording smart label according to claim 1, wherein the communication module is a wireless communication chip and RF antenna; said communication chip operates under a wireless communication protocol in a group consisting of NFC, Wi-Fi (IEEE 802.11), Bluetooth, other radio frequencies, Infra-Red (IR), GSM, CDMA, GPRS, 3G, 4G, W-CDMA, EDGE, DCDMA200, and any combination thereof; and wherein said communication module is configured to generate a communication link with a remote device and transfer usage history, comprising said timestamps of said actuation events recorded in the memory, to the remote device.

7. The usage recording smart label according to claim 1, further comprising one or more power-saving devices selected from either or both of
   an optical detector, configured to activate the power source upon first exposure to light; and
   an insulating tab such that the power source is activated upon removal of said insulating tab from the smart label.

8. The usage recording smart label according claim 1, further comprising an accelerometer configured to sense vibrations of the usage recording smart label simultaneously with the detection signal generated by the capacitive touch sensing plate.

9. The usage recording smart label according to claim 1, further comprising text printed thereon.

10. The usage recording smart label according to claim 9, wherein said text comprises one or more of a drug name, dosage information, and disclosures required by law or regulations.

11. A method for recording usage of an inhaler, comprising the steps of:
    attaching the usage recording smart label according to claim 1 to an inhaler;
    receiving a detection signal having a duration from the capacitive touch sensing plate;
    verifying that the duration of the detection signal exceeds a predetermined duration threshold;
    retrieving the time of the verified event detection signal from the real-time clock; and
    recording a timestamp of an actuation event at said retrieved time of said inhaler in the memory,
    wherein said smart label is in the form of a sticker conformable to an external surface of said inhaler.

12. The method of claim 11, wherein the method further comprises initiating operation of the power source, so that the power source is configured to supply power to the CPU, the touch-sense controller and the real time clock only after said initiation, wherein said initiating is effected by either or both of
    exposing an optical detector of said usage recording smart label to light; and
    removing an insulating tab of said usage recording smart label.

13. The method according to claim 11, further comprising
    receiving an additional said detection signal having a duration from the capacitive touch sensing plate;
    determining the time difference between the recorded actuation event and said additional detection signal; and
    verifying that said time difference is higher than a predefined repeated-use threshold prior to recording said additional detection signal in the memory as an additional said actuation event.

14. The method according to claim 11, wherein the usage recording smart label further comprises an accelerometer and wherein the method further comprises, prior to said retrieving:
    receiving a vibration signal from the accelerometer simultaneously with said receiving the detection signal; and
    verifying that one or more of the following conditions is met:
      the vibration signal exceeds a predefined vibration signal threshold, indicative of an actuation event; and
      the vibration signal matches at least one vibration pattern indicative of an actuation event.

15. The method according to claim 11, further comprising steps of:
  providing a remote device, configured to support the communication protocol;
  generating a communication link between the communication chip and the remote device;
  transferring usage history comprising said timestamps of said actuation events recorded in the memory to the remote device.

16. A usage monitoring inhaler comprising:
  an inhaler, comprising at least one dose of an inhalable pharmaceutical composition; and
  a usage monitoring smart label comprising:
    at least one capacitive touch sensing plate, configured to generate a detection signal in response to sensed proximity of a human organ or parts thereof;
    a touch-sense controller, configured to control the capacitive touch sensing plate;
    a communication module, configured to support at least one wired or wireless communication protocol;
    a memory;
    a real time clock;
    a CPU, connected to the memory, the real time clock, the touch-sense controller and the communication module;
    a power source, configured to supply power to the touch-sense controller, the CPU and the real time clock; and
    a bottom cover comprising an external adhesive layer,
  wherein the CPU is configured to retrieve a detection signal from the at least one proximity sensor capacitive touch sensing plate, verify that the duration of the detection signal exceeds a predetermined duration threshold, retrieve the time of its occurrence from the real time clock, and record a timestamp of an actuation event at said retrieved time of said inhaler, corresponding to the verified detection signal, in the memory; and
  wherein the usage recording smart label is in the form of a sticker conformably attached to an external surface of said inhaler.

17. The usage monitoring inhaler of claim 16, wherein the inhaler is of a type selected from a group consisting of a metered-dose inhaler, dry-powder inhaler, and soft-mist inhaler.

18. The usage monitoring inhaler of claim 16, wherein said inhaler is used for the treatment of a pulmonary disease selected from asthma and COPD.

19. The usage monitoring inhaler of claim 16, wherein said usage recording smart label comprises text thereon.

20. The usage monitoring inhaler of claim 19, wherein said text comprises one or more of a drug name, dosage information, and disclosures required by law or regulations for said inhaler.

21. The usage monitoring inhaler of claim 20, wherein said usage recording smart label is employed as a replacement for an existing label of said inhaler.

22. A replacement label for an inhaler, said replacement label comprising:
  at least one proximity sensor, configured to generate a detection signal in response to touch of a human organ or parts thereof;
  a communication module, configured to support at least one wired or wireless communication protocol;
  a memory;
  a real time clock;
  a CPU, connected to the memory, the real time clock, the proximity sensor and the communication module; and
  a power source, configured to supply power to the proximity sensor, the CPU and the real time clock,
wherein the CPU is configured to retrieve the detection signal from the proximity sensor, verify that the duration of the detection signal exceeds a predetermined duration threshold, retrieve the time of its occurrence from the real time clock, and record a timestamp at said retrieved time of an actuation event of said inhaler, corresponding to the verified detection signal, in the memory;
wherein said replacement label is in the form of a sticker conformably attached to an external surface of said inhaler; and
wherein said replacement label comprises text printed thereon that was printed on a replaced label.

23. The replacement label of claim 22, wherein said proximity sensor comprises a capacitive touch sensing plate and a touch-sense controller.

* * * * *